US012078403B2

(12) United States Patent
Cutting et al.

(10) Patent No.: US 12,078,403 B2
(45) Date of Patent: *Sep. 3, 2024

(54) RAPID FREEZING, STORAGE, TRANSPORT, AND THAWING SYSTEM FOR CONTAINERS OF BIOPHARMACEUTICAL PRODUCTS

(71) Applicant: SARTORIUS STEDIM NORTH AMERICA, INC., Bohemia, NY (US)

(72) Inventors: Jonathan Cutting, New York, NY (US); Marc Sanchez, Cambridge, MA (US)

(73) Assignee: SARTORIUS STEDIM NORTH AMERICA, INC., Bohemia, NY (US)

( * ) Notice: Subject to any disclaimer, the term of this patent is extended or adjusted under 35 U.S.C. 154(b) by 46 days.

This patent is subject to a terminal disclaimer.

(21) Appl. No.: 17/651,672

(22) Filed: Feb. 18, 2022

(65) Prior Publication Data

US 2022/0170694 A1    Jun. 2, 2022

Related U.S. Application Data

(63) Continuation-in-part of application No. 16/153,172, filed on Oct. 5, 2018, now Pat. No. 11,253,430.

(51) Int. Cl.
*F25D 15/00* (2006.01)
*A61J 1/10* (2006.01)
(Continued)

(52) U.S. Cl.
CPC ............ *F25D 15/00* (2013.01); *B01F 31/265* (2022.01); *F25D 17/06* (2013.01); *F25D 25/00* (2013.01);
(Continued)

(58) Field of Classification Search
CPC .......... B01F 31/20; B01F 31/24; B01F 31/26; B01F 31/265; B01F 31/60; F25D 15/00; B65D 2519/00776; B03B 4/02
See application file for complete search history.

(56) References Cited

U.S. PATENT DOCUMENTS 989,783 A  *  4/1911  Jeffris .................. B01F 35/423
                                                          366/212
3,261,394 A  *  7/1966  Foster ..................... F25D 17/06
                                                          165/122

(Continued)

FOREIGN PATENT DOCUMENTS

EP       1 134 000 A2    9/2001
WO      2012/135216 A2  10/2012

OTHER PUBLICATIONS

International Search Report issued for International Patent Application No. PCT/US2019/054554 dated Jan. 29, 2020.
(Continued)

*Primary Examiner* — Christopher R Zerphey
(74) *Attorney, Agent, or Firm* — NIXON & VANDERHYE

(57) ABSTRACT

Disclosed is a system for freezing, storing, transporting, and thawing biopharmaceutical product, comprising a stationary equipment and one or more movable pallets, each pallet configured to carry one or more container units, each containing biopharmaceutical product, the stationary equipment comprising a gas circulating unit configured to cause a circulation of cold gas and/or warm gas, from a pull inlet toward a blow outlet, wherein there is provided at least a first side plenum having one or more gas conveying channel therein, configured to be fluidly coupled to the blow outlet of the gas circulating unit, the first side plenum having a plurality of outlet ports directed toward an interior volume of the pallet, wherein the gas circulates substantially in a horizontal direction in the interior volume of the pallet, and wherein a shaking arrangement is provided.

24 Claims, 9 Drawing Sheets

(51) Int. Cl.
  *A61J 1/16* (2023.01)
  *B01F 31/20* (2022.01)
  *B65D 19/00* (2006.01)
  *F25D 17/06* (2006.01)
  *F25D 25/00* (2006.01)

(52) U.S. Cl.
  CPC .................. *A61J 1/10* (2013.01); *A61J 1/165* (2013.01); *B65D 19/00* (2013.01); *B65D 2519/00776* (2013.01); *F25D 2331/801* (2013.01); *F25D 2400/20* (2013.01)

(56) References Cited

U.S. PATENT DOCUMENTS

| | | | |
|---|---|---|---|
| 4,470,264 A | 9/1984 | Morris | |
| 4,474,020 A | 10/1984 | Freeman | |
| 4,736,592 A | 4/1988 | Ohling | |
| 5,297,234 A * | 3/1994 | Harms | F25D 17/06 |
| | | | 604/114 |
| 5,361,828 A | 11/1994 | Lee et al. | |
| 6,012,384 A | 1/2000 | Badalament et al. | |
| 6,615,908 B1 | 9/2003 | Bosher et al. | |
| 6,960,012 B1 * | 11/2005 | Biber | B01F 35/423 |
| | | | 366/605 |
| 7,017,366 B2 | 3/2006 | Bottom | |
| 7,913,511 B2 | 3/2011 | Meyer et al. | |
| 7,946,124 B2 | 5/2011 | Klysen | |
| 8,783,047 B2 | 7/2014 | Tippmann | |
| 8,919,142 B2 | 12/2014 | Tippmann | |
| 9,008,827 B1 | 4/2015 | Dwarakanath et al. | |
| 9,573,754 B2 | 2/2017 | Ahmed et al. | |
| 9,995,524 B2 | 6/2018 | Sigety et al. | |
| 10,119,774 B1 * | 11/2018 | Kosa | F28F 13/125 |
| 2004/0226309 A1 | 11/2004 | Broussard | |
| 2011/0107784 A1 | 5/2011 | Tippmann et al. | |
| 2013/0111931 A1 | 5/2013 | Grinter et al. | |
| 2017/0247156 A1 | 8/2017 | Chopin, III et al. | |
| 2018/0125754 A1 | 5/2018 | Sanchez et al. | |
| 2018/0320949 A1 | 11/2018 | Tippmann et al. | |
| 2019/0274336 A1 | 9/2019 | Tippmann | |
| 2019/0335771 A1 | 11/2019 | Ruuttu et al. | |
| 2020/0041193 A1 | 2/2020 | Sigety et al. | |
| 2020/0217579 A1 * | 7/2020 | Wurm | F25D 3/10 |

OTHER PUBLICATIONS

Written Opinion of the International Searching Authority issued for International Patent Application No. PCT/US2019/054554 dated Jan. 29, 2020.

* cited by examiner

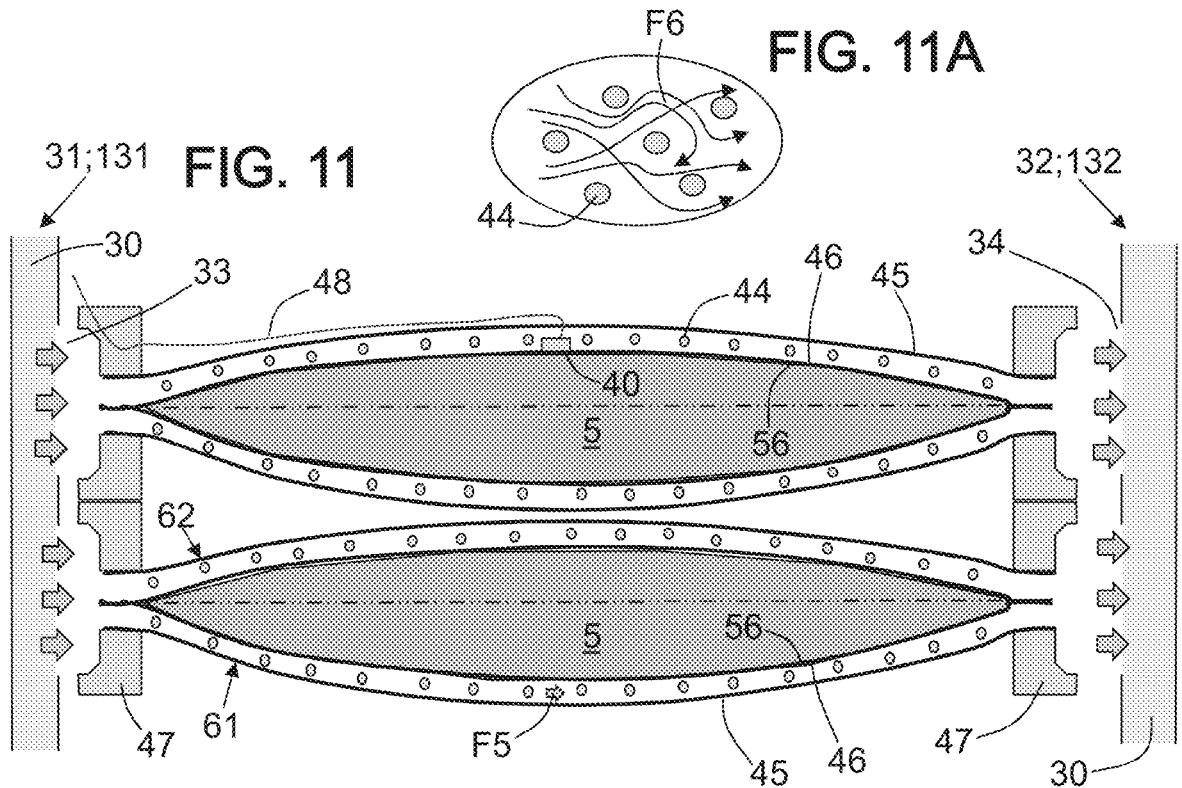
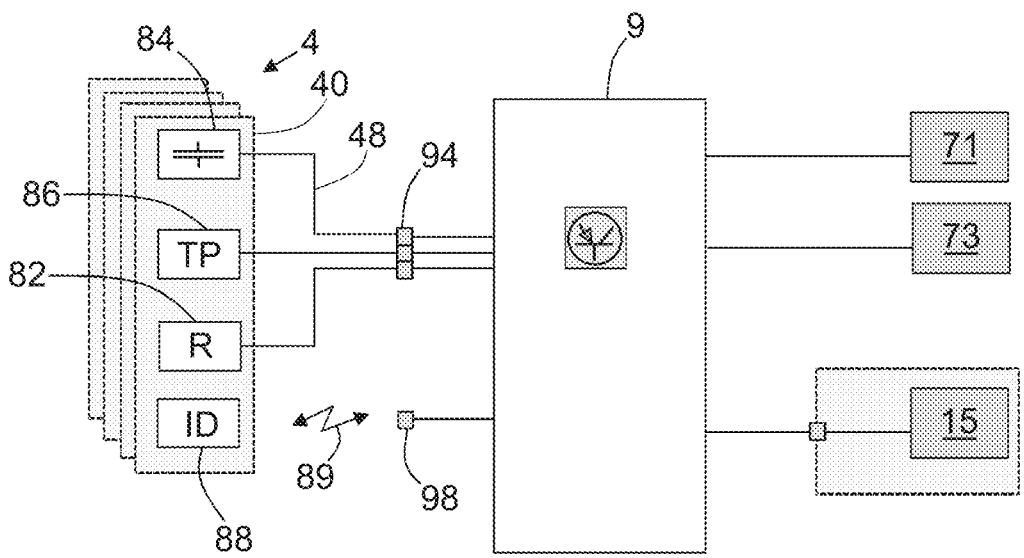

Pallet docketing /coupling

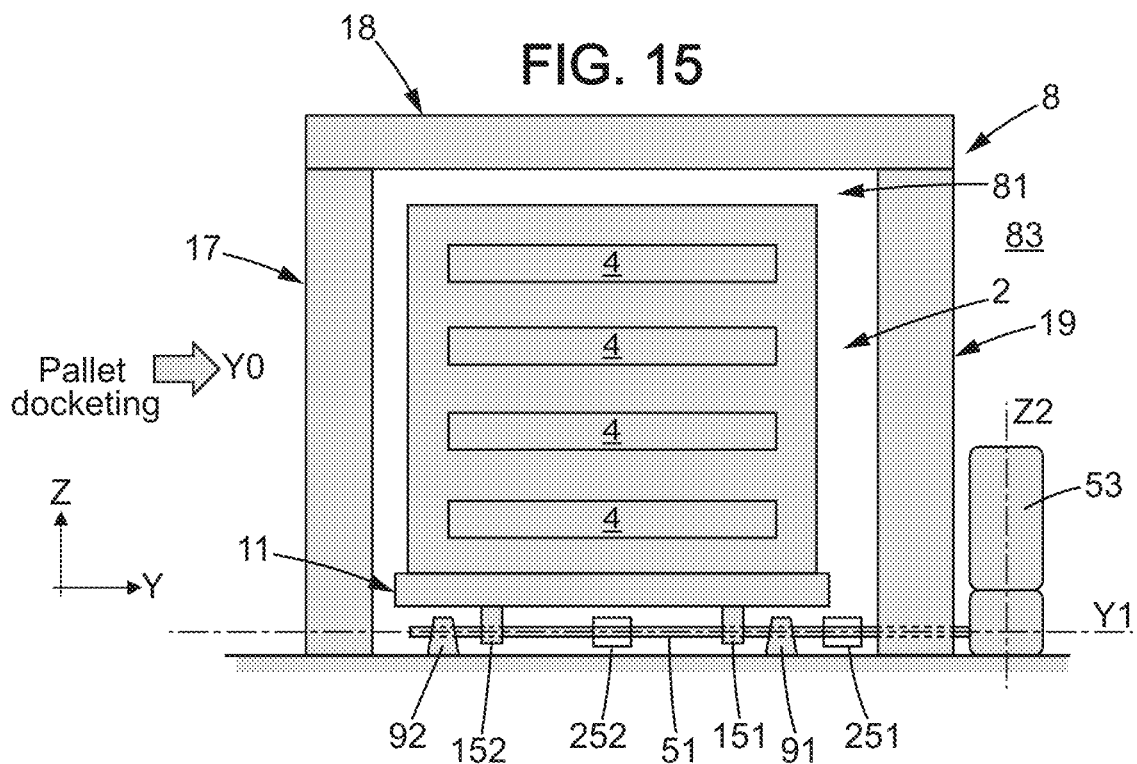
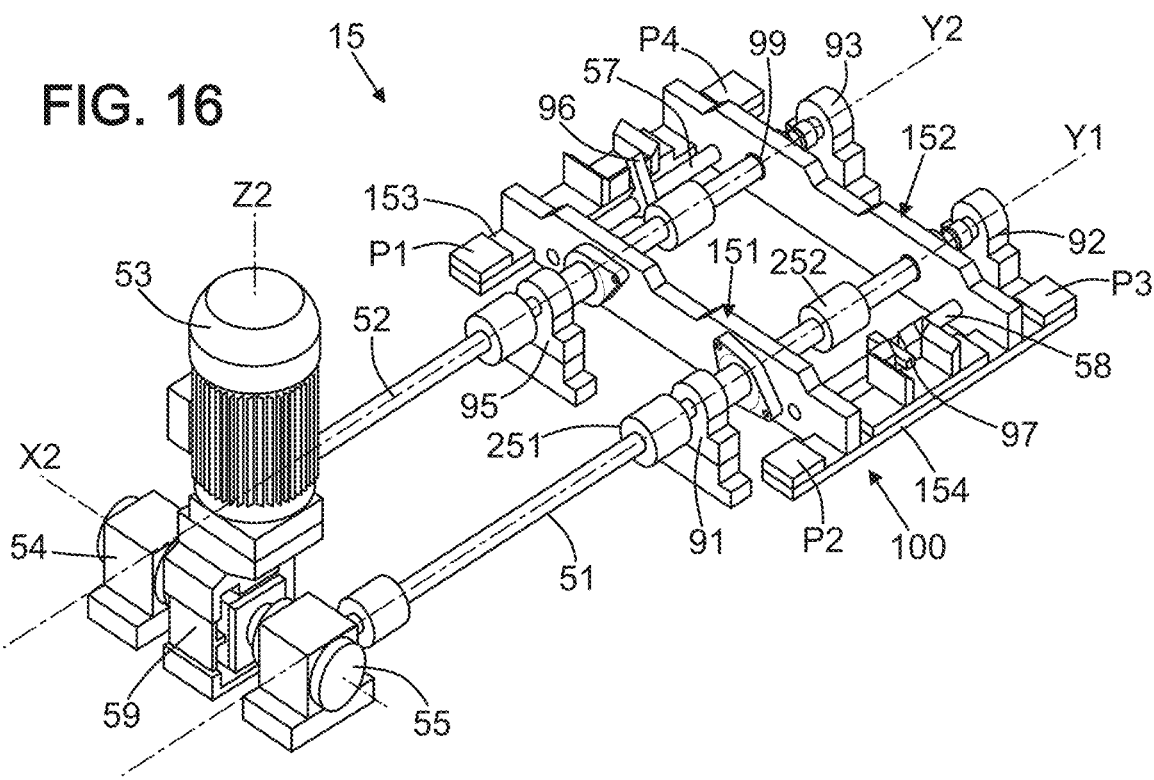

RAPID FREEZING, STORAGE, TRANSPORT, AND THAWING SYSTEM FOR CONTAINERS OF BIOPHARMACEUTICAL PRODUCTS

CROSS-REFERENCE TO RELATED APPLICATION

This application is a continuation-in-part of U.S. application Ser. No. 16/153,172, filed Oct. 5, 2018, and issued as U.S. Pat. No. 11,253,430.

FIELD OF THE INVENTION

The present disclosure relates to a freezing, storage, transport, and thawing system for disposable single-use containers containing biopharmaceutical products. More particularly, the system can be applied to disposable, single-use containers containing biopharmaceutical products.

BACKGROUND OF THE DISCLOSURE

There is a need to transport containers (such as bags or semi-rigid containers) containing biopharmaceutical products from one facility to another facility. One efficient way to keep the products safe and sterile is to ship the products in a frozen state. At a first facility, the containers containing biopharmaceutical products are frozen, and then shipping is carried out, and at a second facility, the containers containing biopharmaceutical products are thawed. Since the containers contain expensive biopharmaceutical products, they must be protected from mechanical stresses and they are therefore enclosed in a casing or likewise packaging during the whole process of freezing, storage, transport, and thawing. However, the presence of the casing slows down thermal exchanges, and this extends the time required to freeze and thaw the bags. Another issue is the segregation that may occur inside the bag during phase change. Also, it is important to keep homogeneity of the biopharmaceutical product during temperature change.

High volume of biopharmaceutical products needs to be processed and known solutions exhibit poor productivity ratings.

Under this perspective, there is a need to propose new solutions to reduce the freezing and thawing time. Promoting homogeneity and preventing segregation is another target to meet.

SUMMARY OF THE DISCLOSURE

According to one aspect of the present invention, there is disclosed a system for freezing and thawing biopharmaceutical product, the system comprising a stationary equipment and one or more movable pallet(s), each pallet being configured to carry one or more container unit(s), each containing biopharmaceutical product, the stationary equipment comprising a gas circulating unit configured to cause a circulation of cold gas and/or warm gas, from a pull inlet toward a blow outlet, wherein there is provided at least a first side plenum having one or more gas conveying channel(s) therein, configured to be fluidly coupled to the blow outlet of the gas circulating unit, the first side plenum having a plurality of outlet ports directed toward an interior volume of the pallet, wherein the gas circulates substantially in a horizontal direction in the interior volume of the pallet.

Thanks to these dispositions, the gas circulation is precisely controlled, in terms of flow and path with regard to the containers to be frozen or thawed. The thermal exchanges between the biopharmaceutical product contained in the container(s) and the gas flow running along the top and bottom sides of the containers can be mastered, and process efficiency can be improved.

It should be understood by 'gas' either simply air or a specific gas combination.

The term 'plenum' shall be understood as synonymous to a manifold, i.e. a part having one or more inner volume(s) or recess(es) that are able to guide a flow of fluid (liquid or gas) from a plurality of inlets (converging flow) to a single outlet, or from a single inlet to a plurality of outlets (diverging flow). Such 'plenum' may be formed in a single integral piece or in several assembled pieces. Such 'plenum' may have a mechanical supportive function or may be deprived of any mechanical supportive function.

Here, the biopharmaceutical product is typically a biopharmaceutical fluid, for example a fluid derived from a culture medium, a cell culture, a buffer solution, an artificial nutrition liquid, a blood fraction, a blood derived component or a pharmaceutical fluid or, more broadly, a fluid specifically designed to be used in the medical field The present disclosure also concerns handling of intermediate products that must be moved during manufacturing.

Here, the container unit can be construed as a container alone stricto sensu or as an assembly made of a container and associated protection means, as it will be discussed later.

According to one option, there may be further provided a second side plenum having a plurality of inlet ports, wherein the outlet ports of the first side plenum are adapted to blow gas while the inlet ports of the second side plenum are adapted to pull gas and return the gas to the gas circulating unit, where the inlet ports are arranged respectively opposite the outlet ports in the horizontal direction. The second side plenum is configured to be fluidly coupled to the pull inlet of the gas circulating unit. Advantageously, a closed loop circuit is provided for the gas circulation, which improves the efficiency and controllability. This also improves the horizontality of the gas flow.

According to one option, the container units may be formed as bag assemblies, each bag assembly comprising a single-use flexible bag and a protective packaging, each single-use flexible bag containing biopharmaceutical product (BP). The protective packaging can be any type of casing, shell or frame substantially surrounding at least the border of the bag. It is therefore possible to handle flexible bags conveniently and safely.

The term 'pouch' can also be used instead of 'bag'. 'Vessel' can also be sometimes used instead or 'bag' or 'pouch'.

The flexible bag (or pouch) is generally designed for a single use and is adapted to contain a biopharmaceutical fluid volume which is here comprised between 5 liters and 100 liters, in some exemplary uses it is comprised between 10 liters and 30 liters. Advantageously this kind of bag, when empty before use, occupies a very small space, it can be flat, folded or even rolled up. Also, in most cases, the weight of the container unit allows a manual handling by qualified personnel without hauling assistance.

According to one advantageous aspect, the container units, respectively the single-use flexible bags, extend substantially in the horizontal direction. Whereby, the container units (resp. the bag assemblies) can be installed in a stable position (i.e. self-standing position), either on supports provided on the pallet or on a stack configuration (stacked on top of one another). This is consistent with horizontal gas flow and this maximizes the thermal transfer surface/area.

According to one option, the system may further comprise a shaker device. Such shaker device can include reciprocating, orbital, or other periodic movement for causing the mixing the content of each container unit. For example, reciprocating movement is imparted to the whole pallet, which improves the homogeneity of the biopharmaceutical product in each container unit (resp. flexible bag). Reciprocating movement can also prevent segregation if such function is required. Shaker can engage with the base of the pallet.

According to one option, there may be further provided turbulators that favor turbulent gas flow along top and bottom sides of the containers. Such turbulators can include baffles. This promotes turbulent flow (versus laminar flow) and serves to break down the boundary layer; this increases thermal exchange coefficient, thereby resulting in a better overall efficiency.

According to one possible choice, the side plenums are arranged on the pallet. Stated otherwise, the one or two side plenums are mounted on the pallet base, via an optional damping/cushioning layer interposed between the pallet base and the side plenums. Under this configuration, the stationary equipment can be made rather compact with no floor occupation. Each pallet has its own plenum(s) with a simple and easy-to-couple interface with the gas circulating unit.

According to another possible choice, the side plenums are arranged on the stationary equipment. This gives a reduced footprint for the pallet(s). This also decreases the capital expenditure since pallets are simpler.

According to one option, the container units may be stacked on top of one another. Whereby, use of a shelf supporting system can be avoided in the pallet.

According to one option, there may be provided local gas guiding walls at top and bottom sides of each container unit. Such local gas guiding walls provide precise guidance of air flow along the bags/containers. Such local gas guiding walls can substantially surround each bag (each container). In the case of bags and protective packaging, appropriate local gas guiding means can be provided in the packaging itself (e.g. in the casing).

According to one option, there may be provided side supports to support the container units. Thereby, several container units (resp. bag assemblies) can be installed independently from one another in a pallet. Having several container units in a pallet enables to process a large volume of product at the same time, with independence concerning handling (it is not necessary to take/handle the top unit first).

According to one option, there may be horizontal separator plates arranged between two neighboring container units to provide gas guidance. Such separator plates are preferably arranged at distance from the container units themselves allowing thereby gas passage. This improves air flow controllability, promotes homogeneous/balanced thermal flow.

According to one option, the stationary equipment (or in practice the gas circulating unit) may comprise a blower, and a heat exchanger. The blower imparts the gas circulation, preferably under controlled speed/flow and the heat exchanger can be for example any air chiller, using a cold source. One example can be a liquid nitrogen exchanger to cool down air, which proves to be an efficient solution to provide cold air. A second example can be a conventional refrigerant-to-air heat exchanger which utilizes the latent heat of an evaporating refrigerant to cool the air.

According to one option, the stationary equipment (or in practice the gas circulating unit) may comprise an electrical heater. This is an efficient solution to provide warm, thawing air/gas and provides good controllability.

According to one option, the gas (i.e air) flow adjacent to the bags/containers is flowing in the same direction at upper side and lower side of the bag. This provides uniform boundary conditions between top and bottom respective portions. Temperature gradient across the thickness of the bag is thereby minimized.

According to one option, there are provided an inlet conduit at the first side plenum and an outlet conduit at the second side plenum for coupling the one or two plenums to the gas circulating unit. Easy coupling/decoupling, preferably obtained by the final approach movement when the pallet is docked to the gas circulating unit.

According to one option, there may be provided a closing cover that can be installed to cover the pallet for avoiding ingress of foreign objects during transport. The cover may have additionally a thermal barrier function.

According to one option, the pallet has a base with grooves for the passage of forklift arms, and easy handling with such forklift.

According to one option, the system may further comprise a control unit and one or more sensors, for monitoring or for controlling the freezing/thawing process in a closed loop fashion.

According to one option, the pallet may exhibit a footprint of substantially 80 cm×120 cm. This is "Euro pallet" standard, which is an affordable base and exhibits excellent availability.

According to one option, there is defined for the pallet a pallet density index $PDI=BPV/PLV$ where BPV is the total volume of the biopharmaceutical product (BP) contained in the container units housed in the pallet, where PLV is the height of the pallet multiplied by the footprint of the pallet (i.e. the overall volume), and wherein PDI is comprised between 0.1 and 0.4, preferably in a range [0.15 to 0.3]. This proves to be an optimum compromise for good usage of volume versus thermal flow efficiency.

According to one option, the protective packaging can comprise a local gas inner guiding wall 46 in contact with the flexible bag, whereby preventing any contact between the circulating gas and the outer surface of the flexible bag, and allowing thermal flow therebetween.

According to one option, the protective packaging can be designed to promote a good contact between the circulating gas and the outer surface of the flexible bag.

According to a second aspect of the present invention, there is provided a pallet configured to be used in a system for freezing and thawing biopharmaceutical product, the pallet being configured to carry one or more container units, each containing biopharmaceutical product, the pallet comprising a first side plenum having one or more gas conveying channel(s) therein, configured to be fluidly coupled to a blow outlet of a gas circulating unit, the first side plenum having a plurality of outlet ports directed toward an interior volume of the pallet, wherein the gas circulates substantially in a horizontal direction (XY) in the interior volume of the pallet.

According to one option, the pallet may further comprise a second side plenum having a plurality of inlet ports, the second side plenum being configured to be fluidly coupled to the pull inlet of the gas circulating unit, wherein the outlet ports of the first side plenum are adapted to blow gas while the inlet ports of the second side plenum are adapted to pull gas and return the gas towards the gas circulating unit, where the inlet ports are arranged opposite the outlet ports in the horizontal direction.

According to a third aspect of the present invention, there is provided a system for freezing and thawing biopharmaceutical product, the system comprising a stationary equipment and a plurality of movable pallets, each pallet being configured to carry one or more protective packaging, each protective packaging being adapted for receiving therein a single-use flexible bag, the stationary equipment comprising a gas circulating unit configured to cause a circulation of cold gas and/or warm gas, from a pull inlet toward at least a blow outlet, wherein there is provided at least a first side plenum having one or more gas conveying channel(s) therein, configured to be fluidly coupled to the blow outlet of the gas circulating unit, the first side plenum having a plurality of outlet ports directed toward an interior volume (CV) of the pallet, wherein the gas circulates substantially in a horizontal direction (XY) in the interior volume of the pallet.

According to one option, the pallet may further comprise a second side plenum having a plurality of inlet port, the second side plenum being configured to be fluidly coupled to the pull inlet of the gas circulating unit, wherein the outlet ports of the first side plenum are adapted to blow gas while the inlet ports of the second side plenum are adapted to pull gas and return the gas towards the gas circulating unit, where the inlet ports are arranged opposite the outlet ports in the horizontal direction.

According to a further aspect of the present disclosure, there is disclosed a system for freezing, storing, transporting, and thawing biopharmaceutical product, the system comprising a stationary equipment (1) and one or more movable pallet(s) (2), each pallet being configured to carry one or more container units (4), each containing biopharmaceutical product (BP), the stationary equipment comprising an enclosure (8) delimiting an inner area (81) and an outer area (83), the inner area being configured to receive one pallet therein, the stationary equipment comprising a gas circulating unit (7) configured to cause a circulation of cold gas or warm gas, from a pull inlet (76) toward a blow outlet (77), wherein the container units extend substantially in the horizontal direction (XY).

whereby the cold gas or warm gas is caused to circulate substantially in a horizontal direction (XY) in an interior volume of the pallet, wherein the system comprises a shaker device (15) comprising one or more strength member (151,152) and a drivetrain, wherein the shaker device is configured to support and shake a pallet present on the shaker device, wherein the drivetrain is configured to impart a periodic movement to the one or more strength member, wherein the drivetrain comprises a motor (53) located in the outer area, one or more drive gear (54,55) located in the outer area, and one or more drive shaft (51,52) located at least partly in the inner area, wherein the drive shaft is in interaction with the one or more strength member.

According to an option, a pallet when present in the enclosure bears directly on the one or more strength member. According to a further option, a pallet when present in the enclosure bears on a frame (100) comprising the one or more strength member, i.e. with indirect support.

It should be noted that the pallet can bear partially on the one or more strength member, directly or indirectly, and partially bear on another member that is not moved via the drivetrain.

According to an option, the interaction between the one or more drive shaft (51,52) and the one or more strength member can be direct or indirect.

Thanks to the arrangement described above, the motor and drive gears are located outside the inner area and do not evacuate heat in the inner area. Also possible chemical pollution possibly generated by the motor and drive gears do not affect the inner area which needs to remain as clean as possible.

According to a further aspect, the periodic movement can be an orbital movement. We thereby provide a gentle shaking without shocks.

According to one option the orbital movement is encompassed in a vertical plane.

According to another option, the orbital movement is encompassing in a horizontal plane.

According to a further aspect, the shaker device may comprise two drive shafts. Thereby there are provided two areas of interaction between the drive shafts and the one or more strength member.

According to a further aspect, the two drive shafts are caused to rotate at the same speed.

According to a further aspect, the system comprises two strength members. This helps supporting a heavy pallet, this also helps distributing the weight of the pallet onto the shaker device.

According to a further aspect, each of the two strength members interacts with the two drive shafts, thereby providing four interaction areas arranged in a square configuration from a top viewpoint. Thereby shaking efforts are well-balanced across the 4 interaction areas.

According to a further aspect, the two drive shafts are synchronized in phase. The two strength members remain parallel to themselves. The pallet base remains horizontal. The bags also remain horizontal. Homogeneity and efficient mixing of the liquid product (BP) are therefore enhanced.

According to a further aspect, the periodic movement can be a circular translational movement. As noted above this circular translational movement can be encompassed in a vertical plane, but it is not excluded to have this circular translational movement encompassed in a horizontal plane. More generally there can be considered a combination of the foregoing to provide a 3D periodic trajectory.

According to a further aspect, each drive shaft may be supported and held by two journal bearings (91,92,93,95). Said journal bearings can bear directly or indirectly on a bottom wall of the enclosure or on the ground. According to one embodiment, there are provided four journal bearings arranged in square configuration from a top viewpoint.

According to a further aspect, each the drive shaft comprises a first portion (51a) and a third portion having a first stationary axis, and a second portion (51b) having a second axis offset with regard to the first axis. Thereby, when the drive shaft is rotated around the first stationary axis, the second axis moves according to a circle around the first stationary axis thereby causing the second portion running the orbital moment.

According to a further aspect, the second axis (Y2) is spaced from first axis (Y1) by an offset distance (EC1) comprised between 10 mm and 25 mm. In other words, this represents the eccentricity provided by the second portion of the driveshaft. According to an option both drive shafts exhibit the same offset distance EC1.

According to a further aspect, there are provided two strength members (151,152), parallel to each other, perpendicular to a pallet introduction direction (Y0). The weight of the pallet is equally distributed on the two strength members.

According to a further aspect, there may be provided a receiving frame (100) comprising the two strength members and two cross members (153,154). This provides a strong and sturdy frame to receive a pallet, notably a heavy pallet.

According to a further aspect, there are provided a clamping device to hold the pallet on the receiving frame. Thereby, once the pallet is installed on the frame and clamped by the clamping device, the shaking movement is reliably transmitted to all the container units supported within the pallet. The clamping device prevents sliding or relative movement of the pallet on the receiving frame.

According to a further aspect, the container units are formed as bag assemblies, each bag assembly comprising a single-use flexible bag (5) and a protective packaging (6), each single-use flexible bag containing biopharmaceutical product (BP).

According to a further aspect, the shaker device is configured to receive and support a pallet exhibiting a weight of at least 300 Kg. In some embodiments, the shaker device is configured to receive and support a pallet exhibiting a weight of at least 400 Kg. For example, the pallet can contain four bags of the 75 litres each.

According to a further aspect, the drivetrain is configured to impart a rotation speed to the drive shaft, said rotation speed being comprised between 40 rpm and 120 rpm. In one embodiment, the rotation speed can be comprised between 55 rpm and 100 rpm. 'Rpm' stands for revolution per minute. This range of rotation speed corresponds to an optimal range for having a good mixing of the biopharmaceutical product contains in the container units without involving too much acceleration level. Homogeneity of the biopharmaceutical product during freezing process can be improved. The same may apply for the thawing process.

According to a further aspect, the stationary equipment may comprise a blower (71), and a heat exchanger (72). The heat exchanger can selectively provide calories (thawing) or take out calories (freezing).

According to a further aspect, the pallet exhibits a footprint of substantially 800 mm×1200 mm. This size of pallet is suitable for housing large container units each containing up to 100 litres each.

According to a further aspect, the receiving frame may comprise at least four pads (P1-P4) to support the pallet. In one embodiment, there may be provided four pads arranged at the corners of the square thereby providing a good stability for receiving the pallet which in turn have four feet at its corners.

According to a further aspect, the receiving frame may comprise six pads (P1-P6) to support the pallet. This improves the distribution of weight on the receiving frame.

According to a further aspect, there are provided two bevel gears (55,54), each interposed between the motor and a drive shaft, each of the two drive shafts (51,52) is driven by a single motor, and each bevel gear is driven by a single motor.

According to a further aspect, each of the two drive shafts is driven at the same rotation speed. According to a further aspect, the two drive shafts are driven in synchronicity, i.e. the phase of the eccentricity of the second axis (Y3) is the same for both drive shafts.

According to a further aspect, the single motor is coupled to a reduction gear (59) having an output shaft interposed between the two bevel gears, the single motor having a vertical axis (Z2), the output shaft exhibiting a horizontal axis (X2) and driving each of the two bevel gears.

According to a further aspect, each of the two drive shafts (51,52) extend over a length (L1,L2) of at least 2 meters.

According to a further aspect, wherein the shaker device exhibits an overall height (H2) less than 200 mm.

BRIEF DESCRIPTION OF THE DRAWINGS

Other features and advantages of the invention appear from the following detailed description of one of its embodiments, given by way of non-limiting example, and with reference to the accompanying drawings, in which:

FIG. 11 is another diagrammatic section view of an exemplary container unit, FIG. 11A is a zoomed view showing turbulators, FIG. 12 is exemplary block diagram of the control system.

FIGS. 15 to 21 illustrate a further embodiment focusing on the shaking function

FIG. 15 is a diagrammatic side view of the pallet in a docking position within the stationery equipment.

FIG. 16 is a perspective view of the pallet in a shaking system, for a rear point of view.

FIG. 17 is a detailed longitudinal view of one drive shaft.

FIG. 18 is a detailed sectional view of one drive shaft.

FIG. 19 is a diagrammatic sectional side view of the stationery equipment without pallet therein.

FIG. 20 is a diagrammatic front side view of the stationery equipment with a pallet therein.

FIG. 21 is a top view of part of the shaking system, showing a particular the receiving frame arrangement.

DETAILED DESCRIPTION OF THE DISCLOSURE

In the figures, the same references denote identical or similar elements. For the sake of clarity, some elements may not be represented at scale.

In the context of the present disclosure, there are provided containers (such as bags or semi-rigid containers) containing biopharmaceutical product (denoted BP) which need to be shipped from one facility to another facility under the frozen form.

Here, the biopharmaceutical product is typically a biopharmaceutical fluid, for example a fluid derived from a biopharmaceutical process, like a culture medium, a cell culture, a buffer solution, a blood fraction, or any fluid specifically designed to be used in the medical field. The biopharmaceutical product at stake can also be any intermediate products that must be moved during manufacturing.

Therefore, at one place, there is a need to freeze such containers (or container units) containing biopharmaceutical product, and after transport, at another place, there is a need to thaw such containers containing biopharmaceutical product, such that the biopharmaceutical product can be used and further processed in the liquid form.

Figure 1:
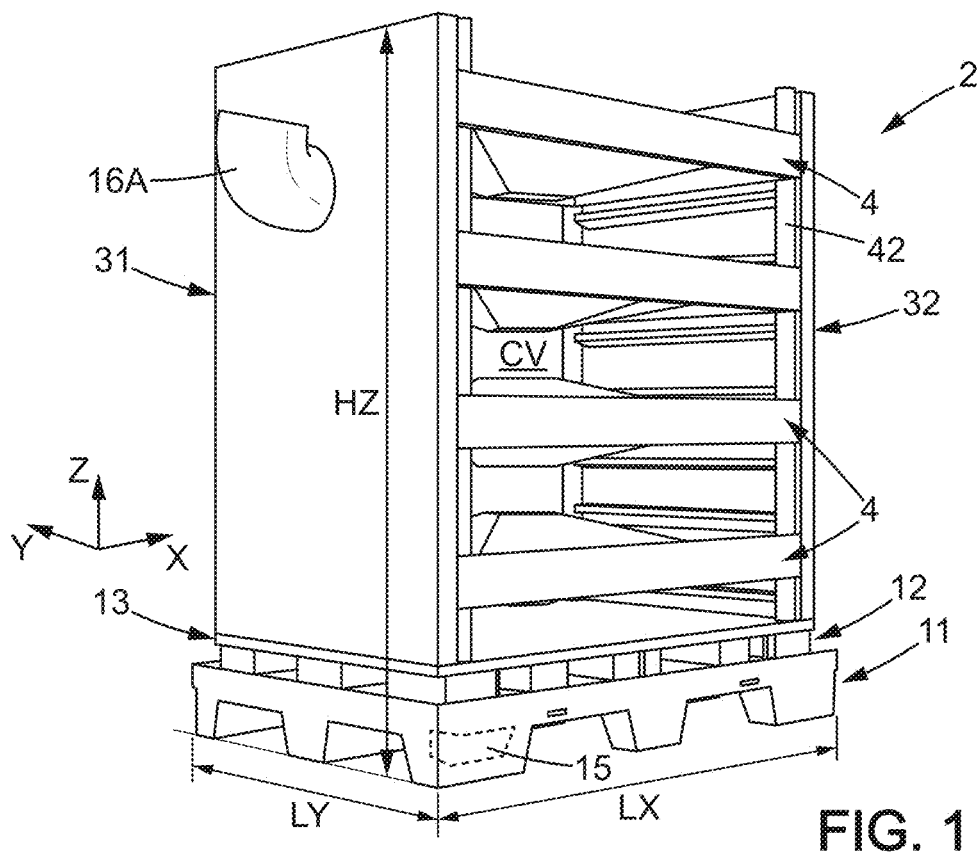
FIG. 1 illustrates a diagrammatic perspective view of a pallet according to a first embodiment.

Freezing, storage, transport, and thawing are performed while the containers are arranged in a pallet 2. As shown in FIG. 1, the pallet 2 comprises a base 11, an optional cushioning/damping layer 12, and optionally a support plate 13. There may be provided additionally a shaker device 15, the latter being described later. The pallet has a base 11 with grooves 11G for the passage of forklift arms, and easy handling with such forklift.

The damping layer 12 can be formed as spaced rubber pads. The support plate 13 can be formed as a thin metal plate, for example from stainless steel.

The pallet 2 exhibits a substantially standard footprint. LY can be 80 cm, LX can be 120 cm. Height HZ can be comprised between 1 m and 2 m, preferably between 1.2 m and 1.6 m The pallet 2 carries one or more container units 4, each containing biopharmaceutical product BP.

Various types of container unit are considered in the scope of the present disclosure. According to one example, the container unit may be formed as a bag assembly 4, each bag assembly comprising a single-use flexible bag 5 and a protective packaging 6, each single-use flexible bag containing biopharmaceutical product BP. The protective packaging can be any type of casing, shell or frame substantially surrounding at least the border of the bag.

In practice, the protective packaging 6 may be formed as two shells in halves 61,62, namely a bottom shell and a top shell. One example of protecting packaging can be found in the published document US2018-125754 from the same applicant.

Figure 2:
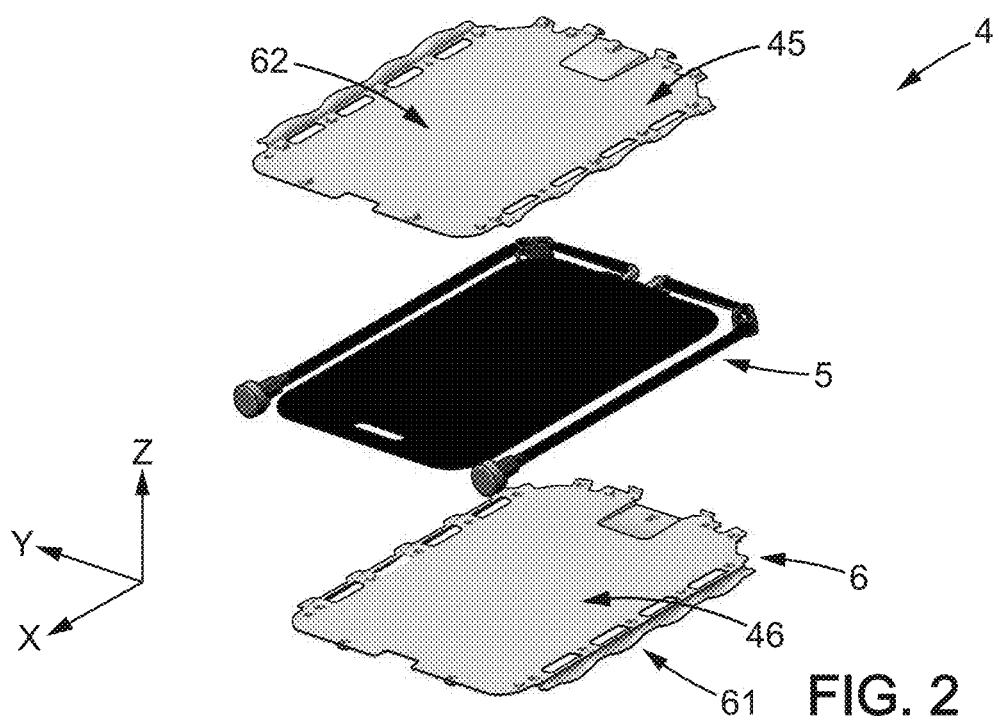
FIG. 2 is an exemplary diagrammatic exploded view of a container unit received in the pallet shown at FIG. 1.

There can be provided a first level of packaging formed as plates as described in US2018-125754, such plates are designed to sandwich substantially the bag 5. Such plates are shown at the FIGS. 2 and 6 by reference numerals 61 and 62.

Figure 6:
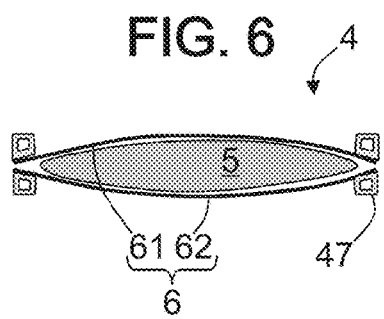
FIG. 6 is a diagrammatic section view of an exemplary container unit.

This first level of packaging can be complemented by a second level of packaging formed as frames 47 which sandwich the plates, as visible at FIGS. 6 and 11. Such frames extend in a peripheral fashion and form strength members or armatures that provide overall rigidity and allow easy handling of the container units 4 in the whole process. Plates and frames can be made of PET or HPDE. More details on plates and frames can be found in US2018-125754.

In one embodiment, there may be provided a hose arrangement for filling and draining the bag, such hose arrangement begin encompassed between the borders of the plates.

Regarding the bags 5 themselves, one can use for example available products like the bag product range Flexboy® from the applicant company Sartorius Stedim Biotech®. Other single use flexible bags can also be used within the context of the present invention.

According to another example, the container unit is formed as a semi-rigid container directly containing the biopharmaceutical product BP. In this configuration, the container unit could be a single container alone, without additional protection means.

In any case, intrinsic protection means or additional protection means allows achievement of a good level of mechanical protection. It is therefore possible to handle flexible bags conveniently and safely.

Protection means also allows to place the container units safely in a horizontal position where they can be in a self-standing and stable state.

Spatial reference is given by horizontal directions X and Y and vertical direction Z. X denotes left-right direction from the forklift user standpoint (from where the pallet is handled with a forklift), whereas Y denotes front-back direction perpendicular to X. We note that docking movement is substantially along Y axis.

In a first embodiment, according to the present disclosure, there is provided at least a first side plenum 31 and a second side plenum 32.

First side plenum 31 extends generally in a YZ plane. Second side plenum 32 extends generally in a YZ plane, but in a position opposite to the first plenum regarding the transverse axis X. First and second side plenums 31,32 exhibit generally a parallelepiped shape. In the shown example, they are generally symmetrical to one another regarding a median YZ plane.

Each side plenum can be manufactured from stainless steel or inert aluminium/tin alloy. Also high performance biocompatible plastics can be used. Also fiber loaded resin or polymer can be used.

Each of first and second side plenums 31,32 has one or more gas conveying channel(s) therein. According to one example, each of first and second side plenums 31,32 can be built as a hollow body. In one example, there is no partition into this hollow body and the overall recess formed by the interior of the hollow body constitutes a single gas conveying channel.

In other embodiments, there may be provided more specific recesses like pipes each forming a specific channel. Even, each of first and second side plenums 31,32 can be formed as a specific manifold.

Here the plenum has a hollow body with two main plates; the plenum hollow body has the plurality of inlet/outlet ports in one of the plate oriented toward the interior volume CV of the pallet and a connection opening for supply (resp discharge) in the other plate oriented toward the exterior of the pallet.

Gas conveying channel(s) of first side plenum 31 convey gas from an inlet duct 16A to outlet ports 33 directed toward an interior volume CV of the pallet.

Gas conveying channels of second side plenum 32 convey gas from plurality of inlet ports 34 to an outlet duct 16B.

In the illustrated example, each outlet port 33 is formed as slot open to the plenum hollow body; the slot extends in the Y direction, and extends substantially along the whole length of the plenum along Y. Instead, there can be provided a plurality through-holes, like nozzles.

At the right side, each inlet port 34 of the side plenum 32 is also formed as slot open to the plenum hollow body; the slot extends in the Y direction, and extends substantially along the whole length of the plenum along Y. There are preferably two slots per container units.

As apparent from the figures, from the forklift user standpoint, the first side plenum 31 is a left side plenum and the second side plenum 32 is a right side plenum. Further, there may be provided a cover 24, delimiting the interior volume CV of the pallet on the top side, the front side and the backside. Stated otherwise, the interior volume CV is delimited on the left and right sides by the plenums 31,32, on the bottom side by the pallet base 11 (or plate 13) and on the remaining sides (top, front, bottom) by the specific cover 24.

The cover 24 is removably installed on the pallet for transport steps. The cover 24 is removed when filling, draining or handling the container units 4. The cover 24 is removed for the freezing and thawing process. The cover 24 provides mechanical protection; it avoids inadvertent ingress of foreign objects in the pallet inner volume CV during transport. In some embodiments, the cover exhibits additionally a thermal barrier function.

Figure 3:
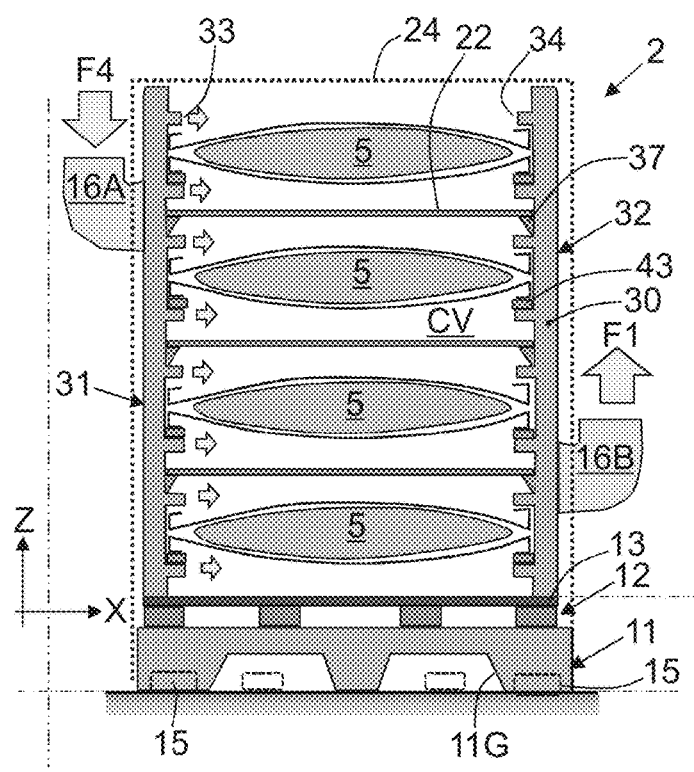
FIG. 3 is a diagrammatic front view of the pallet shown at FIG. 1.
Figure 4:
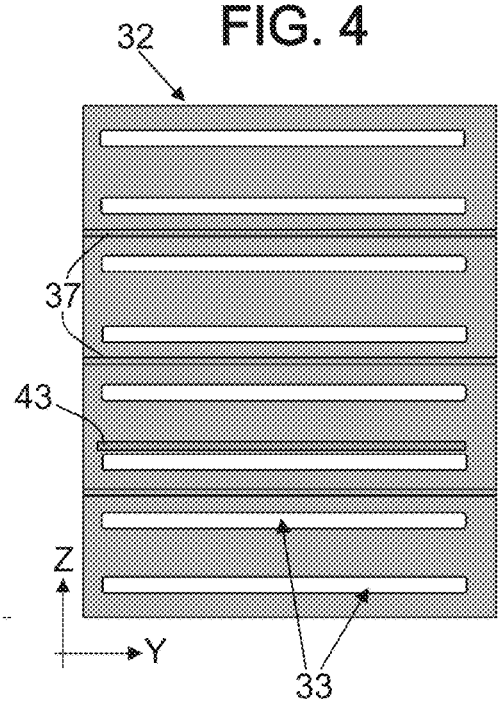
FIG. 4 is an exemplary diagrammatic elevation side view of a plenum used in the pallet shown at FIG. 1.
Figure 5:
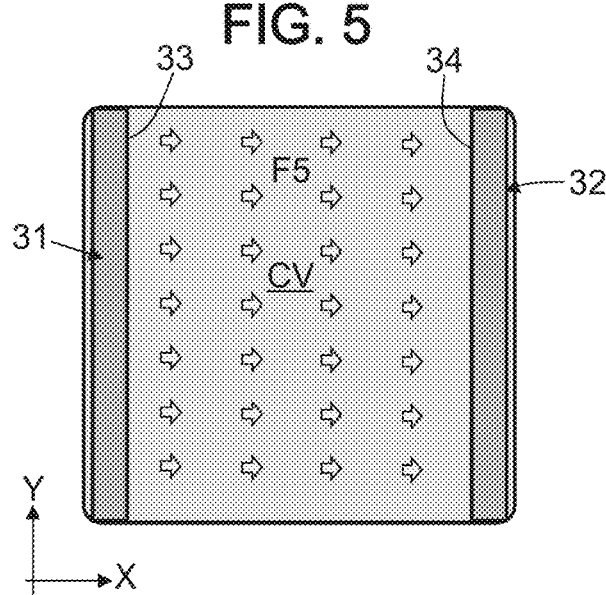
FIG. 5 is a diagrammatic top view of the pallet shown at FIG. 1.

As understood from FIGS. 3, 4 and 5, the gas circulates substantially in a horizontal direction XY in the interior volume CV of the pallet, i.e. from outlet ports 33 of the first side plenum 31 to the horizontally corresponding inlet ports 34 of the second side plenum 32. This horizontal flow is denoted by arrow F5 (FIG. 5).

Figure 7:
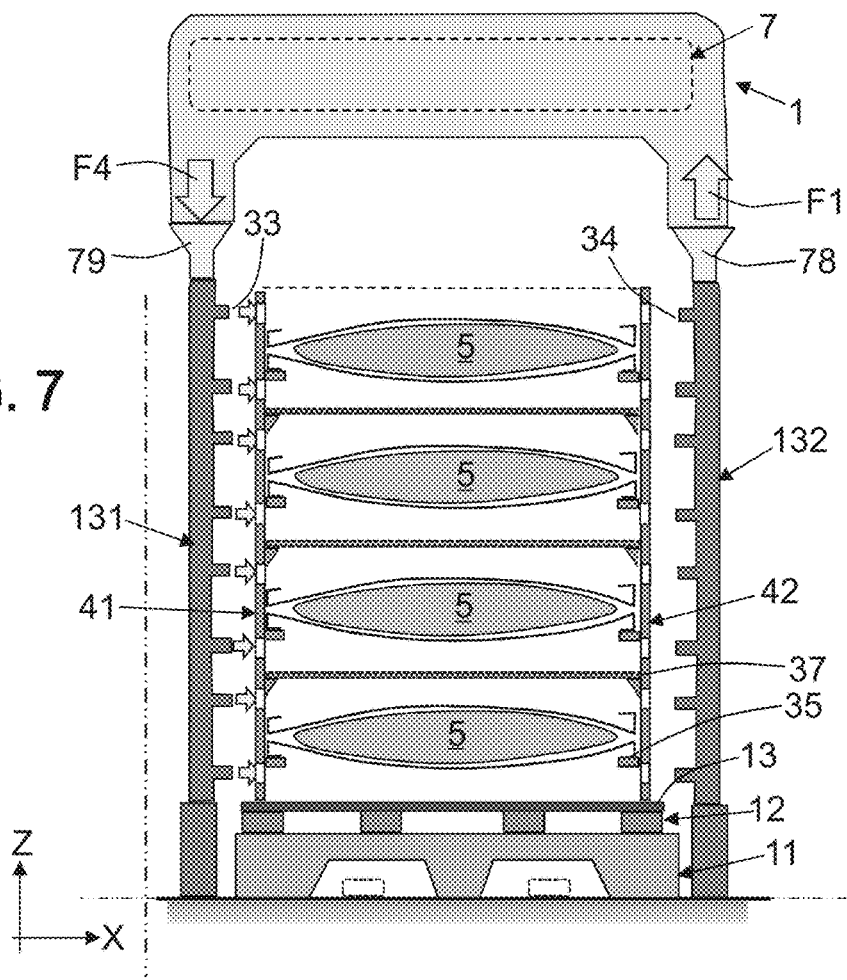
FIG. 7 is analogous to FIG. 3 and illustrates a second embodiment.

Regarding now the way container units 4 are mechanically supported within the pallet, there are considered various solutions. As depicted in FIGS. 1, 3, 7, each container unit is supported on its left and right sides, either directly by the above mentioned plenums or by specific uprights 41,42 (cf FIG. 7).

In other words the above mentioned plenums can comprise therein the upright function or can be deprived of such upright function, in which case the pallet 2 comprises additionally the above mentioned specific uprights 41,42.

Each container unit 4 can be supported on side slides which extend along Y, or by simple shelf supports 43. It is understood that said side slides or simple shelf supports 43 can be arranged directly on the interior side of the plenums or arranged on the specific uprights 41,42.

As understood from FIG. 3, there may be provided additionally horizontal separator plates 22 arranged between two neighboring container units to provide gas guidance. The horizontal separator plates 22 can be arranged on side slides 37 or otherwise on simple shelf supports.

In the case where side slides (resp. simple shelf supports) are arranged directly on the interior side of the plenums, as depicted at FIG. 4, the interior side of the plenums exhibits an alternate succession of outlet ports 33, support 43 for the container units, and side slides 37 for the separator plates 22.

For each container unit 4, there may be provided two outlet ports 33 on the left side plenum, namely one directed to the bottom of the container unit and one directed to the top of the container unit.

In a similar manner, when the second plenum is present, there may be provided two inlet ports 34 on the right side plenum 32, namely one facing the bottom of the container unit and one facing the top of the container unit.

Further, the disclosed system further includes a stationary equipment 1 to which the pallet(s) are to be docked and fluidly coupled.

The stationary equipment 1 comprises a gas circulating unit 7 (not shown at FIG. 1 but illustrated at FIGS. 7 to 10). When it is under operation, the gas circulating unit causes a circulation of cold gas or warm gas (according to the respective need of freezing or thawing), from a pull/suck inlet 76 toward a blow outlet 77.

The gas circulating unit comprises a blower 71, and a heat exchanger 72.

The gas circulating unit comprises an electrical heater 73.

The gas circulating unit is power supplied from electrical network (mains). The pallets are brought in and out from a location situated below the gas circulating unit 7.

Figure 10:
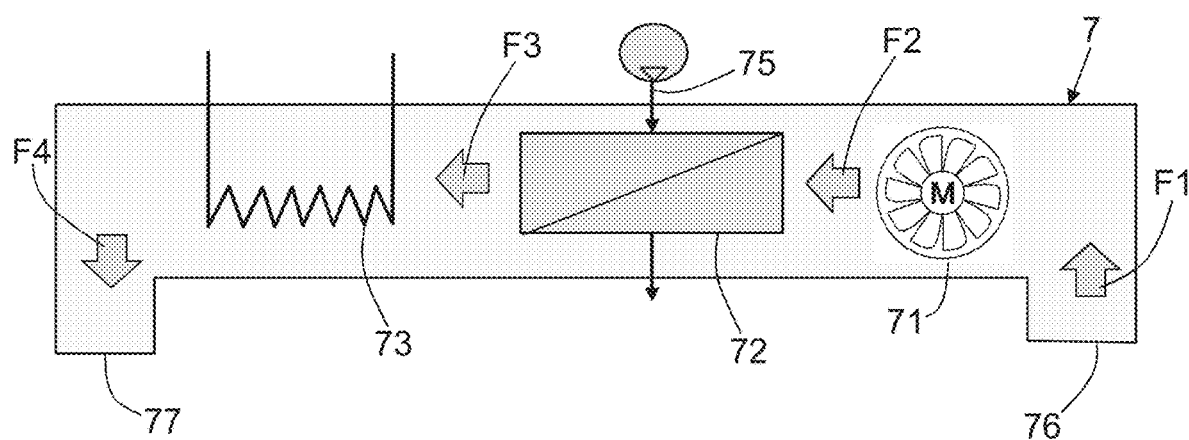
FIG. 10 illustrates an exemplary gas circulating unit.

Regarding the following elements: blower 71, heat exchanger 72, electrical heater 73, various arrangements are possible and the order of these elements from the pull inlet 76 toward to the blow outlet 77 can be different from the one which is illustrated at FIG. 10.

In the shown example, the heat exchanger 72 removes calorie from the air. In practice, it can be in evaporator. Any chilled fluid can be used in the heat exchanger 72 to cool air from F2 to F3 flow sections. Using liquid nitrogen is not excluded. There may be provided a circulation pump 75 to circulate a chilled fluid into the heat exchanger 72.

Air/gas circulates in a channel along a flow shown by arrows F1,F2,F3,F4.

Figure 8:
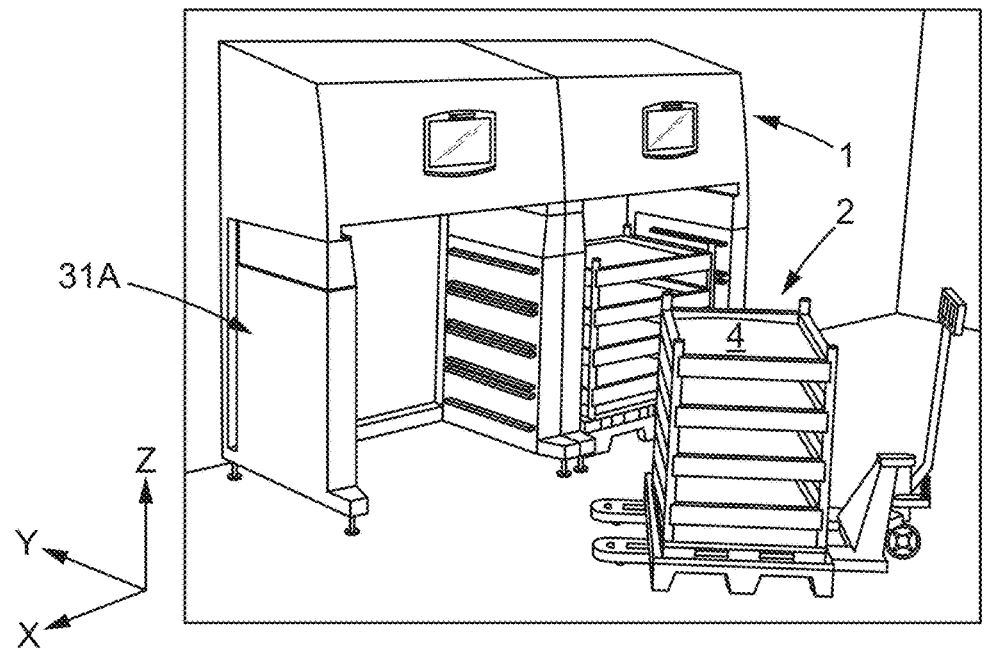
FIGS. 8 and 9 show views of the complete system according to the second embodiment.
Figure 9:
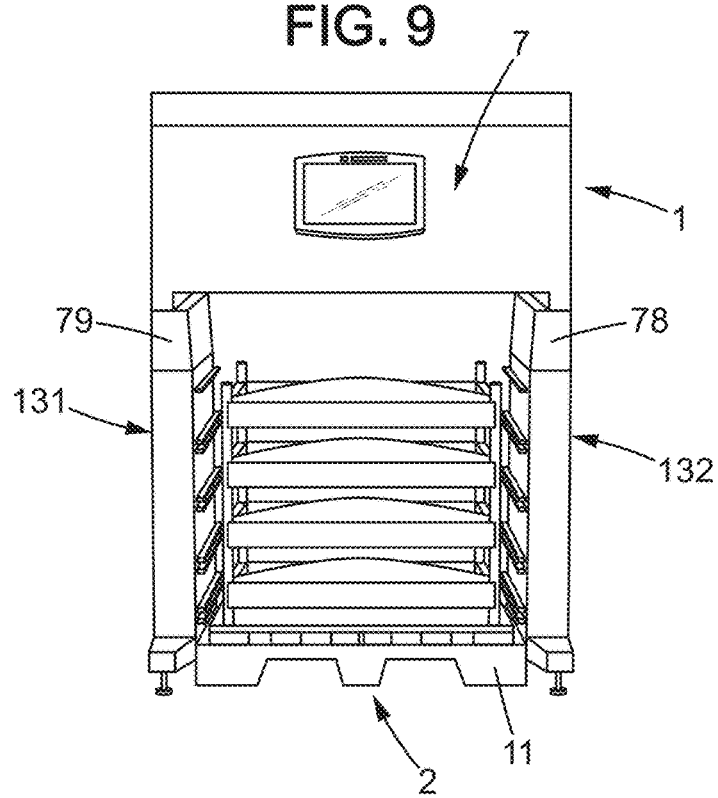

As illustrated in FIGS. 7 to 9, according to a second embodiment, the plenums are not carried by the pallet, by the plenums are stationary. The plenums are arranged as part of the stationary equipment 1. There is provided a first side plenum 131 standing on a socket and connected via a funneling means to the blow outlet 77 of the gas circulating unit 7.

In the illustrated example of FIG. 7, there is provided a second side plenum 132 standing on another socket and connected via a funneling means 78 to the pull/suck inlet 76 of the gas circulating unit 7.

Figure 13:
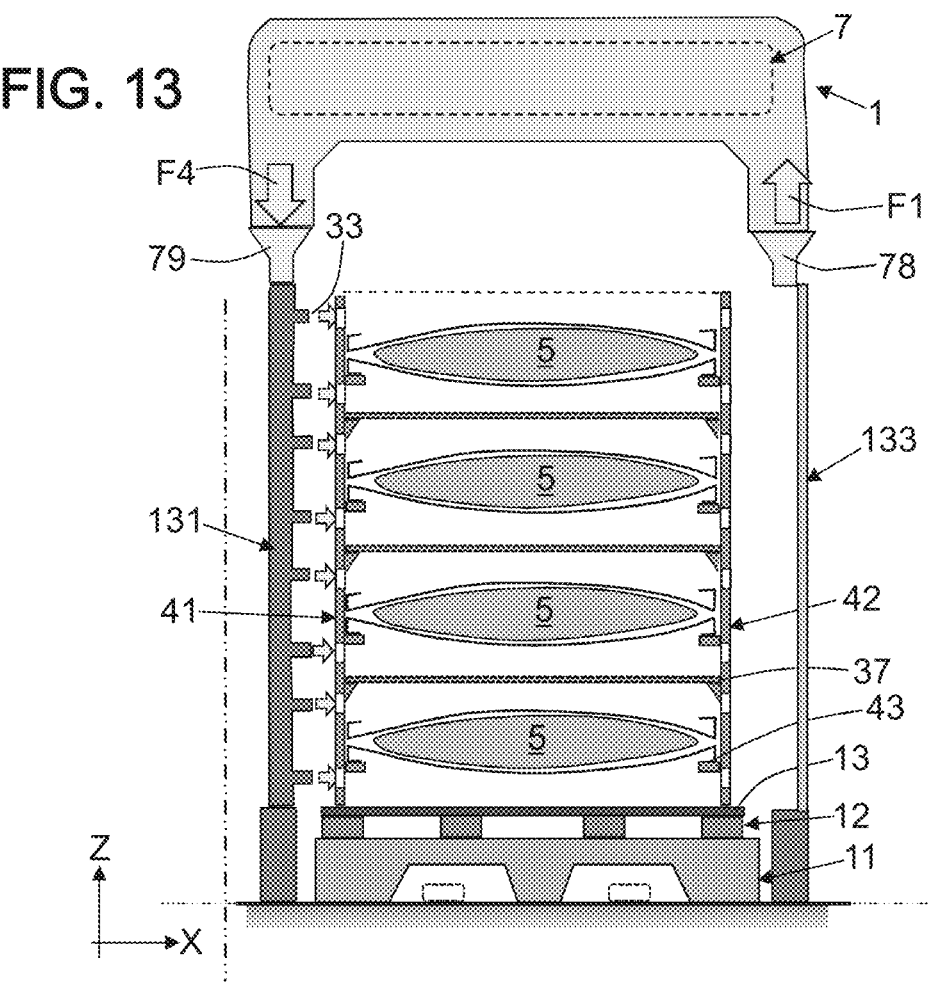
FIG. 13 is analogous to FIG. 7 and shows a variant embodiment.

However, the person in the art can recognize from FIG. 13 that the side plenum 132 is not strictly necessary. The return path from the interior volume CV to the pallet the gas circulating unit 7 can be managed through a simple side wall 133.

The same can apply to the first embodiment where the second side plenum is not strictly necessary.

Gas conveying channel(s) of first side plenum 131 convey gas from an inlet conduit 79 to outlet ports 33 directed toward an interior volume CV of the pallet.

Gas conveying channels of second side plenum 132, when present, convey gas from interior volume CV through the inlet ports 34 and toward the connecting conduit 78.

There is provided a gap between the left upright 41 and the left plenum 31 and a gap between the right upright 42 and the right plenum 32.

It should be noticed that the air flow adjacent to the bags is flowing in the same direction F5 (from left to right at FIGS. 3 and 5) at upper side and lower side of the bag.

There may be further provided local gas guiding walls 45 at top and bottom sides of each container unit, as illustrated at FIG. 11. Such local gas guiding walls may be formed in the protective packaging 6. In other words, the packaging 6 can envelop substantially a gas passage provided along the flexible bag.

Also, in one embodiment, each of the plates 61,62 of the protective packaging 6 can comprise an inner wall 46 and an outer wall 45 delimiting the passage for the gas flow.

According to one optional feature, the inner guiding walls 46 can be designed to prevent any contact between the circulating gas and the outer surface 56 of the flexible bag 5. The inner guiding wall 46 is in contact with the outer surface 56 of the flexible bag thereby allowing conductive thermal flow therebetween to freeze or thaw the biopharmaceutical product BP. Accordingly, the inner guiding walls 46 exhibit low thermal resistance and good thermal conductivity.

According to an alternative feature, the inner guiding walls 46 can be designed to promote a good contact between the circulating gas and the outer surface 56 of the flexible bag 5. In this case, the inner guiding walls 46 can be designed as a grid with a plurality of large through holes.

There may be further provided turbulators 44, which are devices designed to promote turbulent flow F6 along top and bottom sides of the container units. Turbulent flow exhibits a better thermal exchange coefficient than laminar flow. There may be provided baffles or simply an array of rods 44 arranged transversally to the gas flow, as shown at FIG. 11A.

Various solutions are envisioned for turbulators. The rods (or pins or studs) 44 extend between the inner walls 46 and the outer walls 45 delimiting the passage for the gas flow. The rods are arranged in an array and force the air to flow in a meandering path thereby increasing velocity, turbulence, and heat transfer coefficient.

Another solution is described in U.S. Pat. No. 5,361,828A wherein a staggered array of ramp surfaces arranged on inner walls 46 and outer walls 45. Such ramp surfaces promote heat transfer by trailing vortices. This is optimized for flow in a single direction (here F5).

Generally speaking, any protruding or outstanding elements standing across the air passage tends to promote vortices and turbulent flow, which improves the heat transfer efficiency.

As apparent from FIG. 11, the container units may be piled up on one another avoiding use of a shelf supporting system in the pallet. Frame 47 has a generally flat bottom face and has a generally flat upper face, such that the bottom face of one container unit may bear in a stable manner on the upper face of another frame. Such stack configuration can be used both in the first embodiment (plenums on pallet) and in the second embodiment (stationary plenums).

Further, the system comprises a control unit 9 to control the freezing and thawing process. Further, the system comprises one or more sensors 82,84,86. Such sensor(s) provide data which reflects the ongoing freezing process or thawing process.

There may be provided a thermocouple or NTC resistor sensor denoted 82, responsive of a temperature sensed at bag contact.

There may be provided a capacitive sensor 84, which is responsive to the liquid or solid consistence of the biopharmaceutical product, and notably responsive of a phase change of the biopharmaceutical product.

There may be provided a thermopile sensor 86 which is responsive to the liquid or solid consistence of the biopharmaceutical product, and notably responsive of a phase change of the biopharmaceutical product.

Either one or two or three of the above-mentioned sensors can be arranged in a sensing assembly 40. The sensing assembly 40 may be coupled to control unit 9 via one or more wire(s) 48.

The sensing assembly 40 may be arranged in a belly-button position, as shown at FIG. 11.

Further, the system may comprise means for identifying unitarily each container unit. As apparent from FIG. 12, each container unit may carry an identifier ID denoted 88, like for example a RFID chip or a NFC chip. There may be provided a short range reader 98. The short range reader 98 can be located in the pallet or outside the pallet, for example in the stationary equipment. Reading is made via wireless communication 89.

In the components involved in the control system, some of them may be subjected to gamma irradiation for sterility purposes. In particular, the one or more sensors 82,84,86 (possibly as an assembly 40) and the identifier ID 88 may be attached to the bag and form a connectable module subjected to gamma irradiation, whereas the rest of the system is not subject to gamma irradiation. A connector denoted 94 separates the gamma irradiated portion from the rest of the components involved in the control system.

The shaker device 15 can produce an orbital reciprocating movement in the XY plane. The shaker device 15 can produce a to-and-fro movement in the vertical direction Z.

There may be provided one or more shaker device(s) at pallet base 11.

For example, reciprocating movement is imparted to the whole pallet// Each bag assembly.

Figure 14:
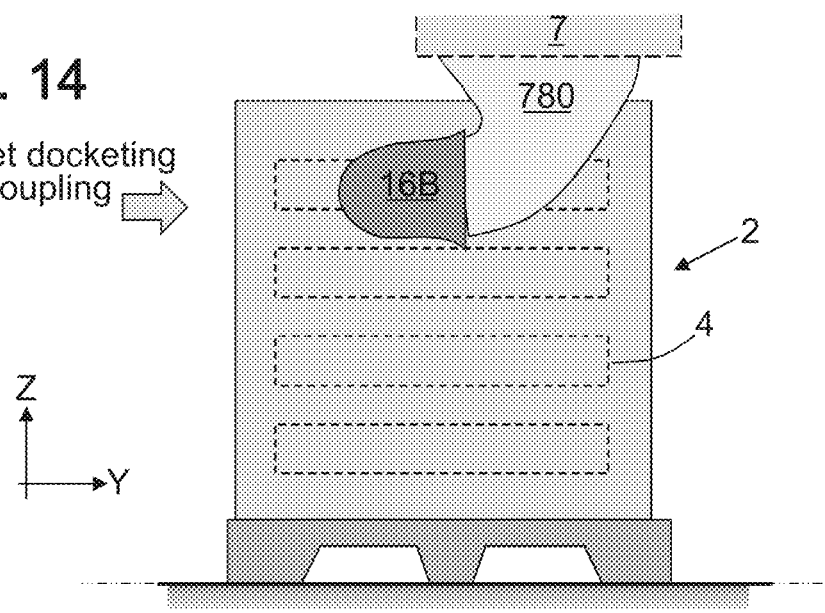
FIG. 14 is a diagrammatic side view of the pallet in a docking position.

FIG. 14 shows a convenient coupling via funnel, together with pallet final move in docking position along the Y direction.

Note: the term 'stationary' does not exclude an equipment that are mounted on rollers and that can be moved if required. But it is not moved for the treatment of pallets.

Regarding the overall arrangement within the pallet, we define for the pallet a pallet density index PDI=BPV/PLV where BPV is the total volume of the biopharmaceutical product BP contained in the container units housed in the pallet, where PLV is the height of the pallet multiplied by the footprint of the pallet (i.e. the overall volume).

The inventors have achieved a density rating with PDI comprised between 0.1 and 0.4, preferably in a range [0.15 to 0.3]. This proves to be an optimum compromise for good usage of volume versus thermal flow efficiency.

Further Embodiment

As illustrated at FIGS. 15 to 21, in a further embodiment, there is proposed a system for freezing biopharmaceutical product in container units. In the following sections, we mainly describe the shaking device, the rest of the system is similar or identical to what was described above.

The stationary equipment comprises an enclosure 8. The enclosure provides thermal insulation notably for the freezing process. There is provided an access door 17 on the front side of the enclosure. Further, there is provided a rear wall 19, a right-side wall 28, a left-side wall 29 and a top wall 18. There may be provided a bottom wall, not illustrated.

We note here that front and rear are conventionally defined with regard to the door 17 and to the introduction of the pallet(s). The same applies for right and left that are taken here from the front door perspective.

The enclosure 8 delimits an inner area 81 and an outer area 83, the inner area being configured to receive one pallet therein. The inner area 81 of the enclosure is generally parallelepiped. The outer area 83 is at room temperature whereas a prescribed temperature prevails within the inner area 81 according to the prevailing operation mode.

The gas circulating unit 7 is not described again here. The gas circulating unit 7 can be located adjacent to the enclosure 8.

The system comprises a shaker device generally denoted 15. The shaker device comprises a drivetrain that will be discussed in detail below. In the illustrated example, the shaker device comprises two strength members, namely a front strength member 152 and back strength member 151. Each strength member is a robust beam extending along the X-axis, perpendicularly to the pallet docking direction Y0 (cf FIG. 15). Each strength member exhibits a generally rectangular cross-section. Each strength member is made of stainless steel or aluminium. In one variant, the strength members can directly support the pallet base 11.

However, in the illustrated example, the strength members form part of a receiving frame 100. In this case, there are provided cross members 153, 154. More precisely there is provided at the right side a first cross member 153 extending along Y (pallet docking direction) and at the left side a second cross member 154 also extending along Y. The first cross member 153 is rigidly fixed/attached to the front strength member 152 and back strength member 151. Similarly, the second cross member 154 is rigidly fixed/attached to the front strength member 152 and back strength member 151. The attachments can be soldered attachments or bolted attachments. Each cross member exhibits generally a rectangular cross-section and is formed as a thick plate. Each cross member is made of stainless steel or aluminium.

The assembly of the two strength members together with the two cross members thereby constitute a robust receiving frame 100.

At the corners of the receiving frame, there are respectively provided four pads P1 P2 P3 P4. This defines generally the footprint of the pallet. In such embodiment, each pallet comprises four feet arranged in geometric correspondence with the four pads of the receiving frame 100.

In the illustrated example, all the weight of the pallet bears on this receiving frame.

Figure 20:
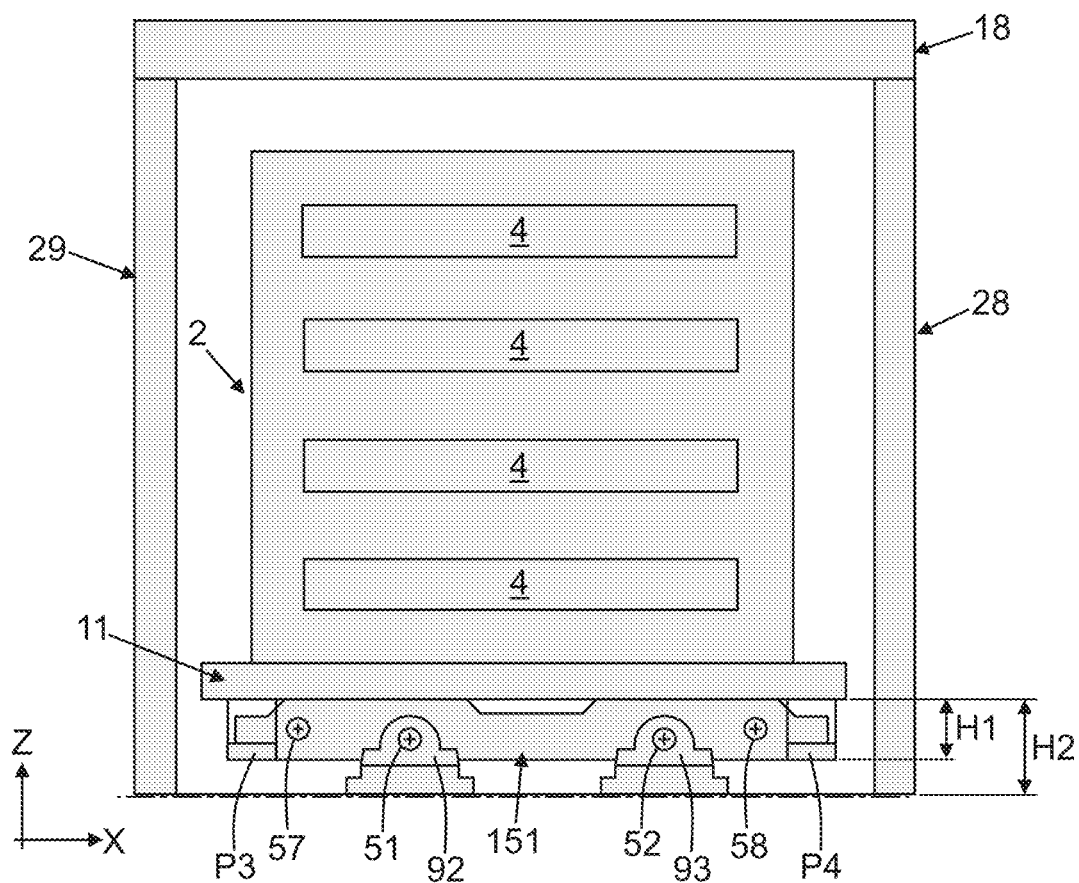

As visible on FIG. 20, the overall height of the frame is denoted H1. In practice H1 is not more than 120 mm. Therefore, the receiving frame has a low profile and does not take a large volume of the inner area 81 of the enclosure. Also, we thereby avoid having to lift/haul the pallet much to install the pallet onto the receiving frame.

Also visible on FIG. 20, the overall height of the shaker device is denoted H2. In practice H2 is not more than 250 mm, preferably less than 20 mm. Therefore, the shaker device has a low profile and does not occupy a large volume of the inner area 81 of the enclosure.

Further, there is provided below the receiving frame some clearance regarding the bottom wall or the ground to allow movement of the receiving frame under shaking condition, notably movement along the vertical direction.

The movement of the receiving frame 100 is imparted by two drive shafts 51,52. Each drive shaft interacts with the two strength members. In the example, each strength members is provided with two bearings 99 in which the respective driveshaft goes through. Low friction sleeves are provided at the strength members bearings 99.

Figure 17:
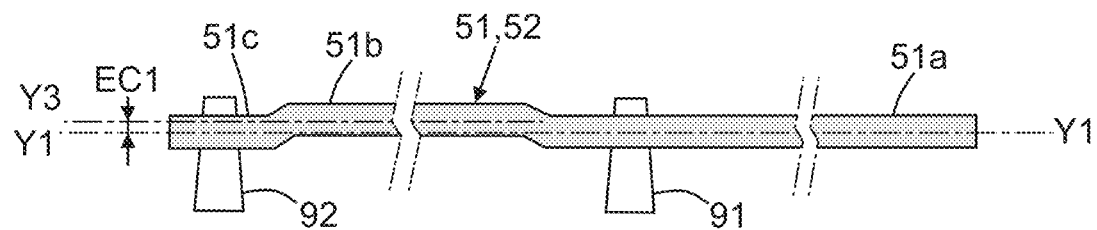

As shown at FIG. 17, each of the drive shafts comprises a first portion 51a and a third portion 51c both aligned and centered with regard to a first stationary axis Y1 (respectively Y2), and a second portion 51b aligned and centered with regard to a second axis Y3 offset with regard to the first axis. The second portion 51b is interposed between first portion 51a and a third portion 51c.

Figure 18:
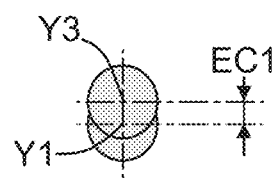

As shown at FIG. 18, distance EC1 between second axis Y3 and first axis Y1 represents the eccentricity of the movement imparted to the second portion 51b.

When the driveshaft rotates, Y3 runs following a circle around Y1. The offset distance EC1 is comprised between 10 mm and 25 mm. Note that the range of movement is equal to 2×EC1.

Each of the drive shafts can be manufactured as an integral part. However in an exemplary embodiment each drive shaft can be made from 2 of 3 parts assembled together by inline joints 251,252.

Each drive shaft may be supported and held by two journal bearings.

Figure 21:
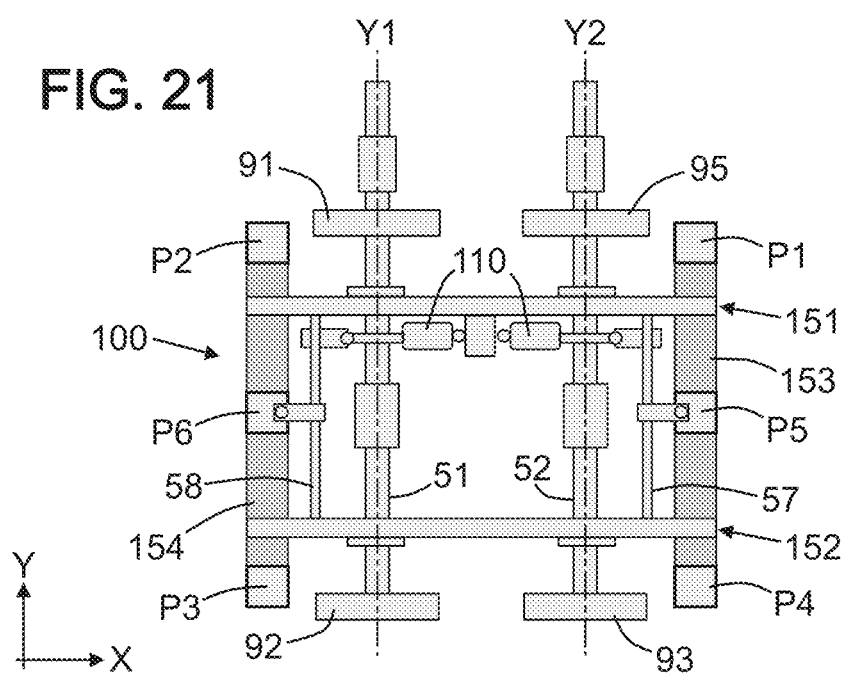

More precisely, with reference to FIGS. 15 and 21, the first drive shaft 51 is supported by journal bearings 91,92, and the second drive shaft 52 is supported by journal bearings 93,95.

There may be provided roller bearings. In exemplary embodiment, sealed ball bearings are used. Alternately, there may be provided low friction sleeves at the journal bearings.

The drivetrain comprises a motor 53, two drive gears 54,55, and the already mentioned two drive shaft 51,52. Here the shaker device comprises a single motor 53. The motor has a vertical axis Z2. The motor 53 is located behind the back wall 19.

The output shaft of the motor is interposed between the two drive gears, the output shaft exhibits a horizontal axis X2. The output shaft of motor 53 drives a reduction gear 59. The reduction gear 59 can be a conventional with pinions train or a worm screw gear, or a planetary reduction gear. The reduction gear 59 is arranged upstream the bevel gears, at the bottom area of the motor 53.

The reduction gear 59 has two output shafts extending along axis X2, driving respectively the two drive gears 54,55.

As shown at FIG. 16, the two drive gears are disposed on either sides of reduction gear 59 along X2 axis.

The drive gears are bevel gears, the output of each bevel gear engages a respective one of the two driveshaft.

The left-hand driveshaft 51 extends along axis Y1 and is driven by the left side bevel gear 55. The right-hand driveshaft 52 extends along axis Y2 and is driven by the right-side bevel gear 54.

Each drive shaft 51,52 is in interaction with the one or more strength member, by means of the second portion of the driveshaft. Each drive shaft 51,52 is received in the above-mentioned strength member bearings 99.

Figure 19:
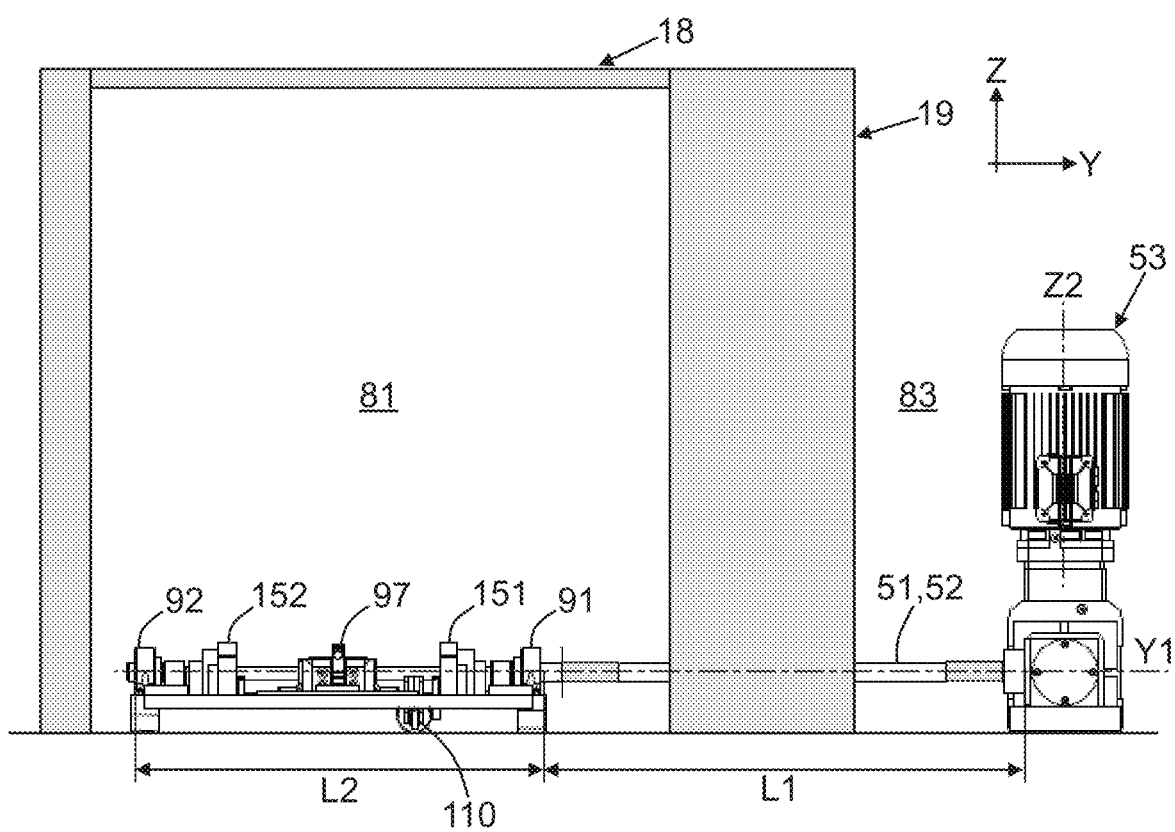

As shown at FIG. 19, in the lengthwise direction of each drive shaft, the length from the respective drive gear to the respective rear journal bearing is denoted L1. The length from the respective rear journal bearing to the respective front journal bearing is denoted L2. L1+L2 is at least 180 cm. in one embodiment, L1+L2 is at least 2 meters.

The drivetrain is configured to impart a drive shaft rotation speed comprised between 40 rpm and 120 rpm, preferably comprised between 55 rpm and 100 rpm. This provides efficient mixing during the freezing process. The motor 53 may rotate in one direction only, with a reference rotation speed of 1500 rpm or 3000 rpm. The reduction gear introduces reduction ratio to slow down and to the desired rpm range between 55 rpm and 100 rpm.

Each of the drive shafts is located at least partly in the inner area 81, and partly in the outer area 83.

Each of the drive shafts go through holes provided in the back wall 19.

The drive gears 54,55 are located in the outer area 83. The motor 53 is located in the outer area 83. Therefore they don't pollute and they do not release heat in the inner area 81.

Further there may be provided a clamping device to hold the pallet securely in place under the action of the shaker device.

For this camping function, there is provided a first auxiliary shaft 58, extending along Y axis interposed between the left side driveshaft 51 in the left side cross member 154. In addition, there is provided a second auxiliary shaft 57, extending along Y axis interposed between the right side driveshaft 52 in the right side cross member 153.

Each of first and second auxiliary shafts 57,58 are rotatably mounted on the strength members 151, 152. A first clamping arm 97 is rigidly attached to the first auxiliary shaft 58.

A second clamping arm 96 is rigidly attached to the second auxiliary shaft 57. Each of first and second clamping arms is movable between a clamping position (Ref 97 FIG. 16) and an open position (Ref 96 FIG. 16). This rotational movement is imparted by an actuator 110 attached to the back strength member 151. Once a pallet 2 is loaded onto the frame 100, a control unit is caused to energize the actuator 110 for moving the clamping arms to the clamping position. The actuator 110 can comprise two pneumatic cylinders selectively pushing or pulling an off-axis projection provided in first and second auxiliary shafts.

A forklift can be used to install a pallet on the receiving frame and retrieve the pallet from the frame after treatment.

There are provided, at the outwards area of the pallet base, a shoulder for a passage of the handling forks of the forklift.

The above sections described a configuration with two strength members and two driveshaft. It is however considered and encompassed in the present disclosure to have only one strength member, and/or to have only one driveshaft.

The invention claimed is:

1. A system for freezing, storing, transporting, and thawing biopharmaceutical product, the system comprising a stationary equipment and one or more movable pallets, each pallet being configured to carry one or more container units, each containing biopharmaceutical product, the stationary equipment comprising an enclosure delimiting an inner area and an outer area, the inner area being configured to receive one pallet therein, the stationary equipment comprising a gas circulating unit configured to cause a circulation of cold gas or warm gas, from a pull inlet toward a blow outlet, wherein a largest dimension of the container unit extends substantially in a horizontal direction whereby the cold gas or warm gas is caused to circulate substantially in the horizontal direction in an interior volume of the pallet, so as to make a horizontal gas flow substantially parallel to said horizontal direction and which maximizes the thermal transfer surface area, such that the horizontal gas flow flows along a top and bottom surface of the container units wherein the system comprises a shaker device comprising one or more strength members and a drivetrain, wherein the shaker device is configured to support and shake a pallet present on the shaker device, wherein the drivetrain is configured to impart a periodic orbital movement in a vertical plane to the one or more strength members, wherein the drivetrain comprises a motor located in the outer area, one or more drive gears located in the outer area, and one or more drive shafts located at least partly in the inner area, wherein the drive shaft is in interaction with the one or more strength members.

2. The system according to claim 1, wherein the periodic movement is an orbital movement.

3. The system according to claim 1, wherein the shaker device comprises two drive shafts (51,52).

4. The system according to claim 3, wherein each drive shaft is supported and held by two journal bearings (91,92, 93,95).

5. The system according to claim 1, wherein the drive shaft comprises a first portion and a third portion having a first stationary axis, and a second portion having a second axis offset with regard to the first axis.

6. The system according to claim 5, wherein the second axis (Y2) is spaced from the first axis (Y1) by an offset distance (EC1) comprised between 10 mm and 25 mm.

7. The system according to claim 1, wherein there are provided two strength members, parallel to each other, perpendicular to a pallet introduction direction.

8. The system according to claim 1, wherein there is provided a receiving frame (100) comprising two strength members and two cross members (153,154).

9. The system according to claim 8, wherein there are provided a clamping device to hold the pallet on the receiving frame.

10. The system according to claim 8, wherein the shaker device is configured to receive and support a pallet exhibiting a weight of at least 300 Kg.

11. The system according to claim 1, wherein the drivetrain is configured to impart a rotation speed to the drive shaft, said rotation speed being comprised between 40 rpm and 120 rpm.

12. The system according to claim 1, wherein the stationary equipment comprises a blower, and a heat exchanger.

13. The system according to claim 1, wherein the pallet exhibits a footprint of substantially 800 mm×1200 mm.

14. The system according to claim 8, wherein the receiving frame comprises at least four pads to support the pallet.

15. The system according to claim 8, wherein the receiving frame comprises six pads to support the pallet.

16. The system according to claim 3, wherein there are provided two bevel gears, each interposed between the motor and a drive shaft, wherein each of the two drive shafts and each bevel are driven by a single motor.

17. The system according to claim 16, wherein each of the two drive shafts is driven at a same rotation speed.

18. The system according to claim 16, wherein the single motor is coupled to a reduction gear having an output shaft interposed between the two bevel gears, the single motor having a vertical axis, the output shaft exhibiting a horizontal axis and driving the bevel gears.

19. The system according to claim 3, wherein each of the two drive shafts extends over a length of at least 2 meters.

20. The system according to claim 1, wherein the shaker device exhibits an overall height (H2) less than 200 mm.

21. The system according to claim 1, wherein the container units are formed as bag assemblies, each bag assembly comprising a single-use flexible bag and a protective packaging, each single-use flexible bag containing biopharmaceutical product.

22. The system according to claim 1, wherein said periodic movement is at least partly in a vertical plane.

23. The system according to claim 22, wherein said shaker device has a receiving frame comprising said one or more strength members and wherein a clearance is provided below said receiving frame regarding a bottom wall or the ground to allow movement of said receiving frame under shaking conditions, notably movement along a vertical direction.

24. The system according to claim 1, wherein said shaker device can engage with a base of the pallet and said periodic movement is imparted to the whole pallet.

* * * * *